United States Patent
Armentano et al.

(10) Patent No.: US 7,363,240 B1
(45) Date of Patent: Apr. 22, 2008

(54) METHOD AND SYSTEM FOR ENHANCED MEDICAL TRIAGE

(75) Inventors: Vincent Armentano, Glastonbury, CT (US); Carol Demumbrum, Redington Shores, FL (US); Russell Steingiser, Glatonbury, CT (US); Stanley Grivers, Jr., South Windsor, CT (US); Lisa Lawton, Naugatuck, CT (US); Julie Morgan, Lyme, CT (US)

(73) Assignee: Travelers Property Casualty Corp., Hartford, CT (US)

( * ) Notice: Subject to any disclaimer, the term of this patent is extended or adjusted under 35 U.S.C. 154(b) by 977 days.

(21) Appl. No.: 10/084,326

(22) Filed: Feb. 28, 2002

Related U.S. Application Data (60) Provisional application No. 60/342,856, filed on Dec. 28, 2001.

(51) Int. Cl.
G06Q 40/00 (2006.01)
G06Q 10/00 (2006.01)
A61B 5/00 (2006.01)

(52) U.S. Cl. ............................................ 705/4; 705/2
(58) Field of Classification Search ............... 705/2–4, 705/8, 9; 600/300
See application file for complete search history.

(56) References Cited

U.S. PATENT DOCUMENTS

| | | | |
|---|---|---|---|
| 2001/0044735 A1* | 11/2001 | Colburn et al. | 705/4 |
| 2002/0069089 A1* | 6/2002 | Larkin et al. | 705/4 |
| 2002/0138306 A1* | 9/2002 | Sabovich | 705/3 |

OTHER PUBLICATIONS

AIG tackles claims management, Apr. 1999, National Underwriter, vol. 103 No. 15, p. 32.*

* cited by examiner

*Primary Examiner*—C. Luke Gilligan
(74) *Attorney, Agent, or Firm*—Irah H. Donner; Wilmer Cutler Pickering Hale and Dorr LLP (57) ABSTRACT

The present invention relates to a method and system for enhanced medical triage in managed care plans that streamlines the conventional medical triage process and referral logic, sends only those insurance claims to an integrated case management system that require medical intervention, matches claims to the right resource at the right time, reduces the time needed to review lost time cases, lessens the number of unnecessary referrals or re-referrals, and further tailors the assignment process of medical insurance claims to medical personnel based on specific market and/or employer dedication.

53 Claims, 4 Drawing Sheets

METHOD AND SYSTEM FOR ENHANCED MEDICAL TRIAGE

CROSS-REFERENCE TO RELATED APPLICATIONS

This application claims priority to and incorporates by reference in its entirety U.S. Provisional Patent Application No. 60/342,856 entitled, "METHOD AND SYSTEM FOR ENHANCED MEDICAL TRIAGE," filed Dec. 28, 2001.

BACKGROUND OF THE INVENTION

1. Field of the Invention

The present invention relates to the field of medical triage for health care plans, and more particularly, to a method and system for automated medical triage in a workers compensation plan.

2. Description of the Related Art

As is known in the art, medical triage is the act of categorizing or classifying patients (e.g., ill or injured persons) according to the severity of their health conditions and thereby determining who need services first. With rising health care and workers compensation costs, medical triage was designed to maximize and create the most efficient use of scarce managed care resources in medical personnel, medical facilities, and the like. While medical triage commonly occurs in emergency rooms, it can occur in other health care settings such as managed care organizations, workers compensation insurance, health care plans, and health care provider systems to steer patients away from more costly care and provide more appropriate services. For instance, medical triage can be used to steer a child with a cold away from an emergency room to preserve the latter for actual medical emergencies. Indeed, these health care organizations and systems have set up "triage centers" to serve as an extension of the utilization review process, as diversions from emergency room care, or as case management resources.

In the current medical triage environment for a managed care program, such as workers compensation (WC), a work injury claim is first called in from an employer of the injured worker (IW) to a telephone reporting center of a workers compensation insurance carrier or health care plan provider. The health and/or workers compensation insurance or care provider may have one or more telephone reporting centers handling the initial claim reportings. The telephone reporting center then performs logistic data collection and entry of information relating to the claim, such as the name of the injured person/worker, social security number of the worker, the employer's address and plant location of the accident and description of the accident. The collected claim information relating to the injured worker and the accident is then transferred out of the telephone reporting center to a local claim service center, (also known as an adjusting field office or AFO) via a claim management system (e.g., T-MATE of Travelers), wherein the AFO is a triage center of the health and/or workers compensation insurance or health plan provider. As with the telephone reporting center, there may be more than one local claim service center.

At the local claim service center, a case or claim handler is assigned to the claim. Part of the normal case set up of the case handler is to review the basic facts from the collected claim information and contact the injured worker to obtain additional facts and the injured worker's description of the accident. The case handler also contacts the employer to verify the information originally obtained by the telephone reporting center from the employer. Additionally, if a physician had provided medical care to the injured worker, the case handler also seeks out the physician to obtain the physician's diagnosis or prognosis of the injured worker and his/her injury. After completing the aforementioned inquiries, the case handler documents the additional facts along with the originally collected claim information, and sends via a system interface, to a medical case manager (MCM). The MCM's task is to review the set of facts and—based on his/her professional opinion as an MCM—determine whether the return-to-work (RTW) time for the injured worker can be impacted. For instance, if the injured worker is to be out for 30 days, can he/she return to work earlier (e.g., in 20 days) if additional medical attention is given; or if the RTW time is 19 days, can he/she come back in 14 days. There are certain instances where the RTW time cannot be impacted, such as when the injured worker was already back at work after the accident and when the worker suffered a fatal injury in the accident. If the MCM judges that the RTW time will not be impacted, the MCM will document a non-referral into the nurse's integrated case management system (ICMS). However, if the MCM judges that the RTW time can be impacted, the MCM will open a medical referral and assignment for the injured worker in ICMS. The assigned nurse will then co-manage the claim with the claims adjuster (i.e., MCM), and work with the appropriate physicians to provide the necessary medical attention and treatment plan to expedite the recuperation of the injured worker and shorten the RTW time. This is because for workers compensation, it is the workers compensation carrier, or self-insured employer, that pays for the medical treatment of the injured worker along with the indemnity payment (i.e., wage replacement) to the injured worker while he/she is not able to work. Thus, it is in the interest of the workers compensation carrier to accelerate and pay a little more on the medical treatment and impact the RTW time of the injured worker in order to cut down on the higher cost of indemnity payment.

BRIEF SUMMARY OF THE INVENTION

There are a number of problems associated with the current medical triage environment. Firstly, it requires the claims routing from T-MATE to ICMS to be "triaged" by the medical unit and its MCMs. The triage process required a review of the medical protocols and assignment by a MCM if lost time is expected to exceed a predetermined amount of time, e.g., 14 days. Because all medical referrals are triaged to determine if medical assignment is warranted in the current ICMS/medical assignment process, it has been found that, on average, a large percentage (48%) of the claims sent to the ICMS were assigned for medical management. It also has been found that there were wide disparities at the AFO level in the medical referrals and assignments sent to the ICMS. For instance, there was a wide variance of assignment percentage and inconsistent application of assignment procedures, wherein assignments by diagnosis and severity of injury vary by office, and a significant number of inappropriate referrals were sent to the ICMS. This is despite the fact that the MCMs are given criteria for medical referrals, such as those shown in Appendix A. Secondly, because an MCM's decision of nurse assignment is based partly on his/her individual experience on the job, turn-overs of MCMs further add to the disparities in the medical triage process. New MCMs with little or different knowledge will have different decisions on medical referrals from those of the more experienced MCMs. Thirdly, there is a huge operational cost in retaining MCMs, whose jobs are solely to determine whether a nurse can add value to workers compensation claims; thus, each office has costly medical resource allocated to the triage function.

Therefore, there exists a need for a method and system for enhanced medical triage in managed care plans, such as workers compensation, that streamlines the triage process and referral logic and sends only those claims to the ICMS that require medical intervention, e.g., by a nurse, thereby changing from an ICMS "triage roster" to an "assignment roster" (ICMS roster). Because each employer has unique claims that need to be properly managed when there is a major impact on medical management, there also exists a need for a method and system for enhanced medical triage that match claims to the right resources at the right time.

Accordingly, the preferred embodiments of the present invention provide a method and system for an enhanced medical triage that provides focused medical intervention, reduces the time needed to review lost time cases, lessens the number of unnecessary referrals or re-referrals, and further tailor the assignment process to medical personnel, such as nurses, based on specific market and/or employer dedication.

The preferred embodiments of the present invention also provide a method and system for an automated medical assignment process that eliminates the need to "triage" and assign claims based on anticipated disability timeframes, and only those claims meeting the medical assignment logic, or manually referred claims, can be routed to the ICMS "assignment roster" for medical assignment.

The preferred embodiments of the present invention also provide a method and system that implements sophisticated referral logic and professional skills for managing health care and/or workers compensation claims to the best outcome.

The preferred embodiments of the present invention further provide a method and system for an automated medical triage through system identification of claims requiring medical management.

The preferred embodiments of the present invention additionally provide a method and system for gathering the collective experience of triage personnel, establishing consistent assignment of selected injury types with high severity and/or potential for impact by a nurse, reducing or eliminating the staff resources required to triage claims, and developing improved claim data collection for future analysis.

Additional aspects and novel features of the invention will be set forth in part in the description that follows, and in part will become more apparent to those skilled in the art upon examination of the present disclosure.

BRIEF DESCRIPTION OF THE DRAWINGS

The preferred embodiments are illustrated by way of example and not limited in the following figures, in which.

DETAILED DESCRIPTION OF THE INVENTION

| Acronyms | |
|---|---|
| AFO | Adjusting Field Office |
| APV | Average Paid Value |
| CAT | Catastrophic claim/severe injury |
| CB | Claim Benefit |
| CM | Claim Medical |
| CM-Plus | Claim Medical-Plus (medical involvement) |
| ICD-9 | International Classification of Diseases, Ninth Revision |
| MIRA | Micro Insurance Reserve Analysis |
| NCCI | National Council on Compensation Insurance |
| NOA | Nature of Accident |
| NOI | Nature of Injury |
| NOL | Notice of Loss |
| POB | Part of Body |
| SAC | Special Account Communication |
| TT | Temporary Total disability |
| TP | Temporary Partial disability |

Figure 1:
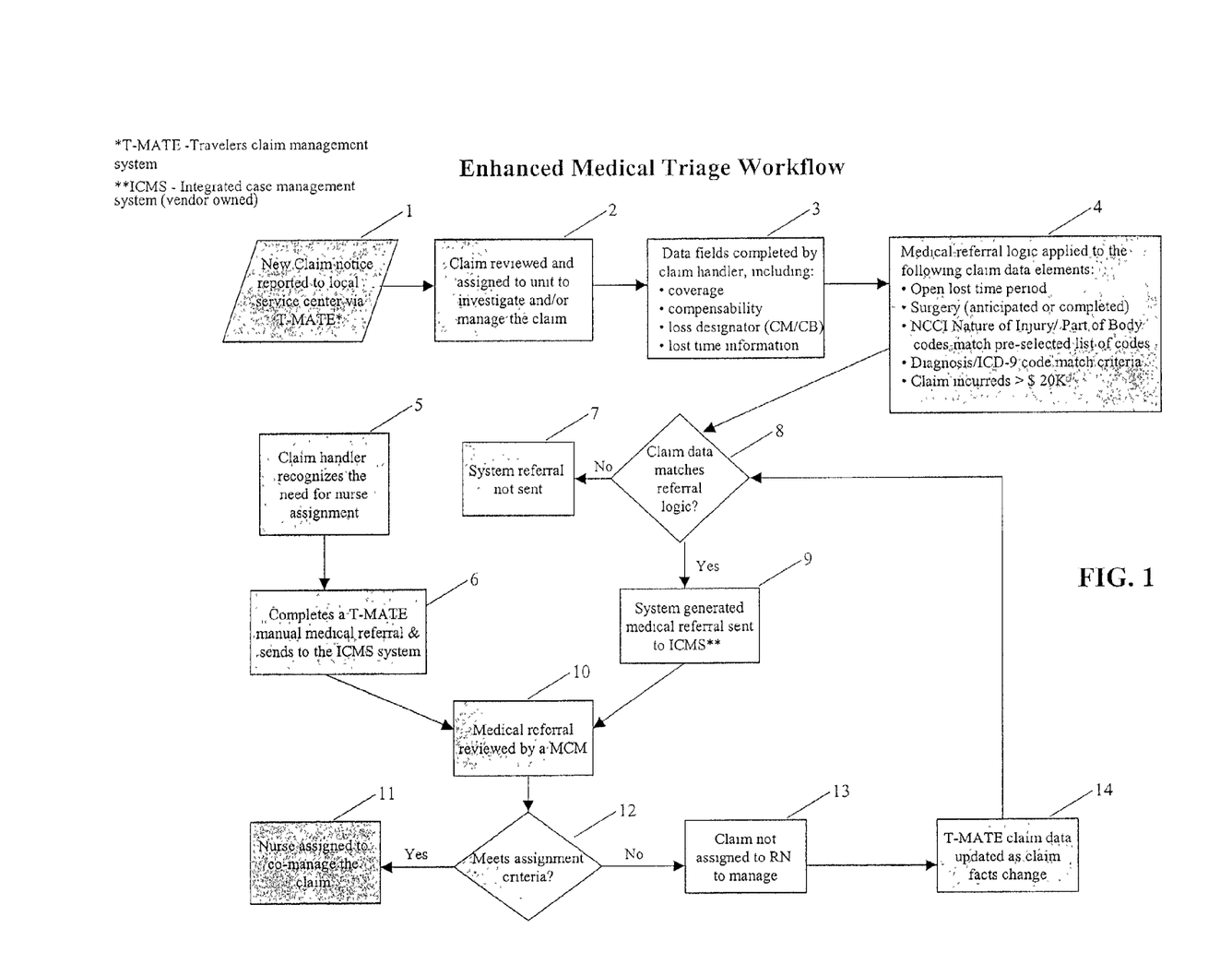
FIG. 1 depicts the enhanced medical triage workflow logic in accordance with one embodiment of the present invention.

Reference is now made in detail to an embodiment of the present invention, an illustrative example of which is illustrated in the accompanying illustrations, showing a method and system for enhanced medical triage that automates and streamlines the medical triage process. FIG. 1 shows the enhanced medical triage, i.e., medical referral/assignment, workflow logic in accordance with the preferred embodiments of the present invention. The enhanced medical triage includes both automated and manual medical referrals/assignments, as will be explained later. The goals and benefits to the streamlined medical assignment logic of the present invention include: 1) early medical intervention; 2) reduction in the amount of time required to review the ICMS roster; 3) reduction in the amount of unnecessary referrals to the ICMS roster; 4) improved consistency in the medical assignment of those claims that will benefit from medical intervention, such as assignment based on potential severity and ability to reduce lost time days; 5) ability of claim handlers to send manual referrals to medical assignment (i.e., manual medical referral/assignment); 6) system documentation of referral objectives for all medical assignments; 7) addition of medical assignment and closure measurements which allow future enhancements to the process; and 8) a re-write and clarification of SAC instructions impacting the medical assignment process, and need for pre-approval of certain services—thus allowing the host insurance carrier or health care plan provider to meet customer specific requests for medical assignment, such as the selection of an outside medical vendor. The current ICMS/medical referral and assignment process include the common triage/assignment decision points shown in Appendix A and the following settings:

All lost time/CB claims are automatically sent to the ICMS roster for triage when claim compensability is accepted;

A review of all CB claims by the medical team (i.e., the medical team "triaged" the claims) to determine if medical assignment will favorably impact the claim outcome by reviewing claim notes, injury type, and anticipated lost work time in excess of a predetermined period of time (e.g., RTW time >14 days);

Early intervention by the MCM; and

Re-referral of a claim by the claim handler, when there is a new disability period, when further medical services are warranted.

The present invention uses much of the above same initial logic that is in the current ICMS/medical referral and assignment process, and builds upon such logic for an enhanced medical triage workflow by preventing non-covered & controverted claims from referring to ICMS. Thus, FIG. 1 shows that steps 1-3 are similar to the current process. At step 1, a new claim notice is reported to a local claim service center (AFO) from a telephone reporting system via a claim management system, such as T-MATE. Although the name "T-MATE" is used throughout the disclosure, it should be understood that any claim management system with equivalent functionality to T-MATE can be used in its place. At step 2, the claim is reviewed and assigned to a claim handling unit, with one or more claim handlers, to investigate and/or manage the claim. At step 3, the claim handler assigned to the claim performs the normal case set up as discussed earlier and collects claim related information such as coverage, compensability, loss designator (e.g., as a CM or CB claim), and lost time information. This information is then used as input to the medical referral/assignment logic of the present invention, as shown in step 4. The formulation of this medical referral/assignment logic is described next.

Figure 2:
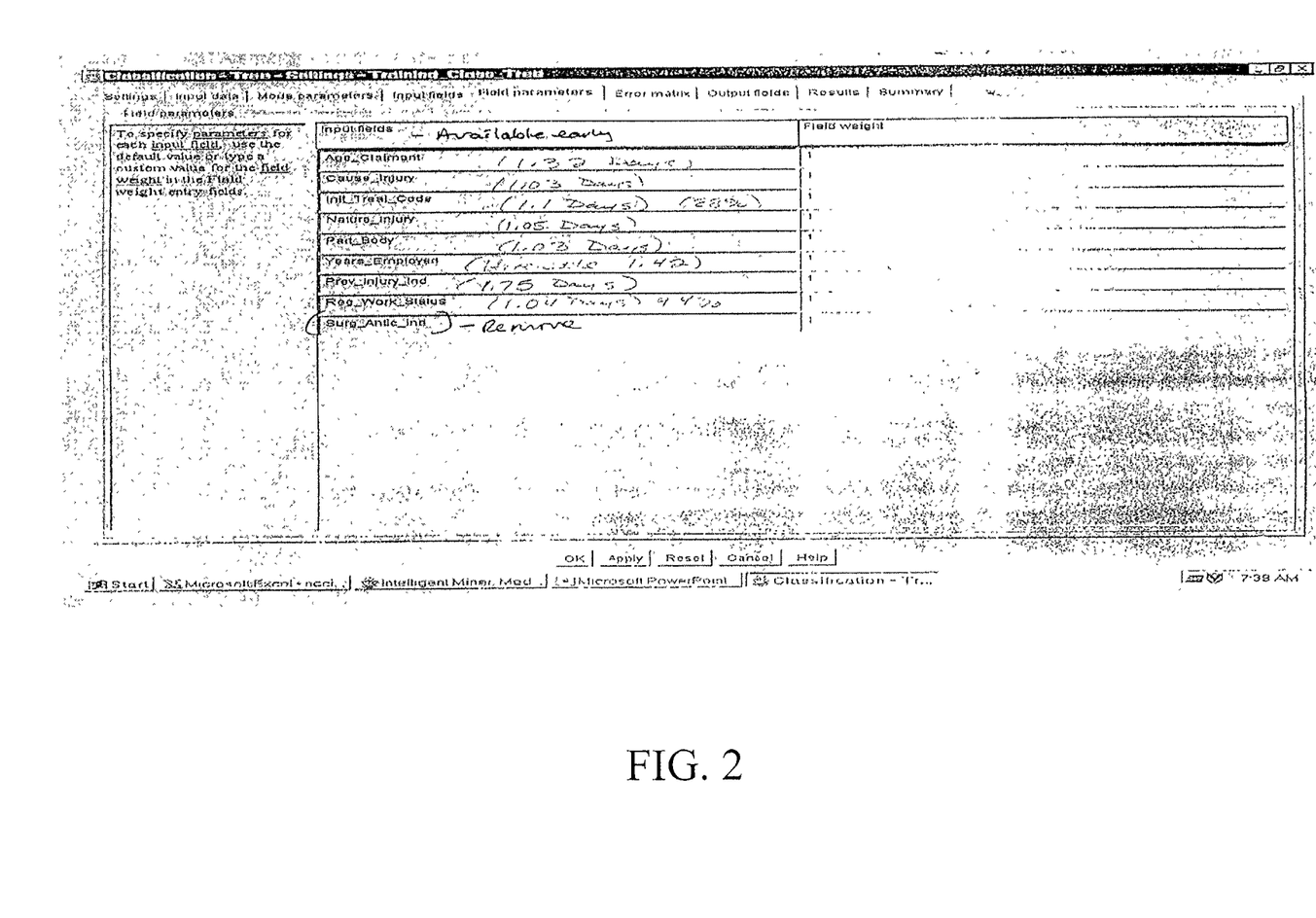
FIG. 2 depicts a sample screen used for collecting/mining the data elements necessary for the medical assignment logic in accordance with an embodiment of the present invention.
Figure 3:
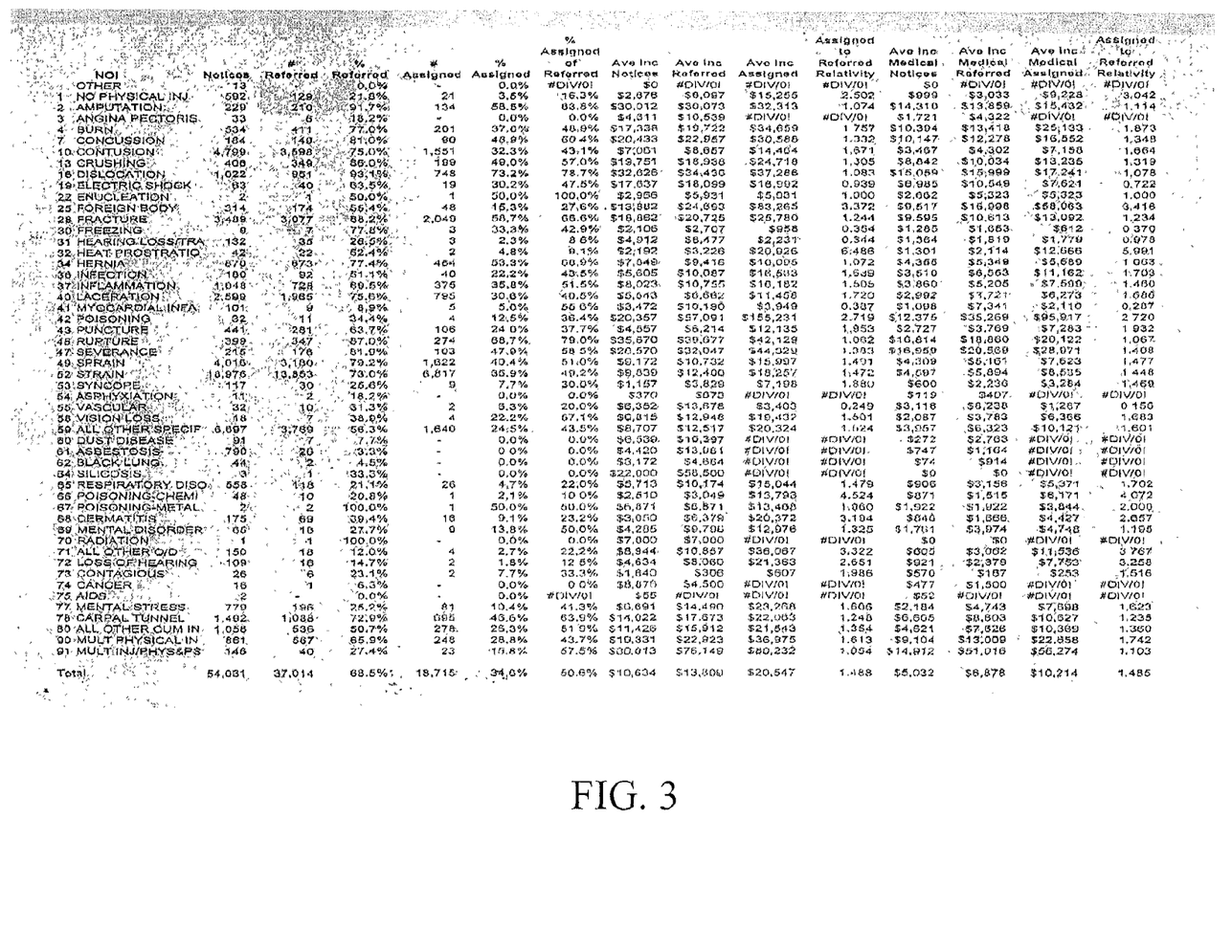
FIG. 3 depicts data mining results as viewed with the NCCI NOI/POB codes match.

According to preferred embodiments of the present invention, the T-MATE to ICMS referral & re-referral logic of the current ICMS/medical referral and assignment process is reviewed by soliciting feedback from all medical team leaders in the local claim service centers (AFOs) as to: a) current methods of claim evaluation to determine medical assignment; and b) SAC instructions that impact the medical assignment decisions. Additionally, a complete analysis is done on medical claims (e.g., workers compensation claims) currently being referred and assigned for medical management and claims non-intervened for medical assignment. This includes: a) finalizing a list of AFOs/service centers to pull data on assignments; b) finalizing a list of data elements that will be captured from the list of AFOs for data mining; c) setting up and completing code to capture the data elements; and d) completing a review of test files for data mining. The AFOs are chosen and finalized based on their claim volume and their current practice of adhering to the conventional manual medical triage process described earlier. Data elements are chosen and finalized based on current, reliable data fields captured in T-MATE that are considered to have an impact on determining medical assignment. Further detailed review included financials (APV, medical and indemnity incurreds), NCCI code combinations, ICD-9 data of assigned and non-assigned claims, anticipated surgery indicator, lost time days, and data mining to determine when certain data elements are populated. The list of data elements for mining includes but is not limited to those shown in Appendix B, with some of the data elements representing a grouping of data. FIG. 2 shows a sample screen used for collecting/mining the data elements. FIG. 3 shows an example of the data mining results of NOI. Appendix C shows an example of the data mining results, where the "average" column denotes the number of days to completion of the data field, the "count" column denotes the claim count, and the "percent" column denotes the percentage of claim files with data field populated.

Based on the data mining results, it is determined that injury codes alone do not drive the medical assignment/referral decision. It is often the injury plus any red flag factors such as those listed in Appendix A. Accordingly, a streamlined medical referral and assignment logic is developed based on factors that most significantly impact the claim assignment to medical care. These factors are in turn based on a combination of the data mining results and the actuarial/financial/manual analysis described above. All of these factors may be considered for initial referrals and re-referrals, and they include:

A) A combination of selected NCCI codes to include both NOI and POB, a list of which is shown in Appendix D. Refer/re-refer when the claim matches one of the selected NCCI NOI/POB codes. ICMS will then display a referral objective as shown in Table 2.

B) Refer/re-refer when the "anticipated surgery" indicator has a value of A (anticipated), P (performed), or B (both anticipated & performed). ICMS will then display a referral objective as shown in Table 2.

C) Refer/re-refer when there is a new date which disability began as entered by the claim handler. ICMS will then display a referral objective as shown in Table 2.

D) Refer/re-refer a claim when actual lost time exceeds a predetermined period of time, e.g., 14 days (i.e., initial lost days). ICMS will then display a referral objective as shown in Table 2. All claims are included, not just the selected NOI/POB codes shown in Appendix D. One time event—only refer/re-refer once. Here, the claim handler and/or the MCM completes the RTW date and qualifier as soon as the injured worker (IW) returns to work to avoid unnecessary referrals to ICMS.

E) Refer/re-refer when the sum of the TT incurred, TP incurred, and medical incurred values (i.e., total cost of all three) is greater than a predetermined amount of money, e.g., $20,000, and there is an open disability. TT denotes temporary total disability, wherein the IW is totally disabled from work temporarily; TP denotes temporary partial disability, wherein the IW is partially disabled from work temporarily, i.e., the IW cannot perform his/her job fully but can perform some form of work. In other words, a referral/re-referral will occur each time that the claim incurreds are greater than $20,000. ICMS will then display a referral objective as shown in Table 2.

F) Refer/re-refer if a selected ICD-9 code or early strategic intervention (ESI) ICD-9 code is processed through the medical bill re-pricing system in which all medical bills are input for payment and possible re-adjustment of payment due to state fee schedule or negotiated network rates. In other words, referral/re-referral logic will look at all of ICD-9 codes stored (primary, plus most recent codes stored) and create a referral/re-referral if any of the stored codes match the selected or ESI codes. The ICD-9 logic includes two distinct groups of ICD-9 codes that may run through the ICMS referral/re-referral logic to create an automated referral. Thus, the referral/re-referral occurs when there is a change of ICD-9 code that matches the criteria of the ICD-9 codes in these two distinct groups, which are:

1. ICD-9 codes that are associated with potential ESI claims (ESI ICD-9 codes), as shown in Table 1; and
2. ICD-9 codes which identify claims with significant medical issues that require medical intervention (selected ICD-9 codes), a sample list of which is shown in Appendix E.

TABLE 1

| ESI Diagnosis | ICD-9 Code |
| --- | --- |
| RSD | 337.9 |
| Multiple Sclerosis | 340 |
| Thoracic Outlet Syndrome | 353.0 |
| Psychiatric Disorder | 300.9 |
| Substance Abuse: ETOH | 305 |
| Substance Abuse: Drugs | 305.9 |
| Chronic Pain | 729.5 |
| Post Traumatic Stress Disorder | 309.89 |
| Organ Transplant - V Code | V43 (996.8 complication of transplanted organ) |
| Toxic Exposure | 980-987 depending upon type of substance |
| Electrocution | 994.8 |
| Post Concussion Syndrome | 310.2/850.9 |
| Failed or multiple back surgeries | 724.9 |
| Rape/Assault | 959.9 |

For the first distinct group, i.e., the ESI ICD-9 codes, there may be an automated ICMS medical assignment/referral of the claim when the ICD-9 code of the claim matches the ESI ICD-9 codes used by the major case unit (MCU). The MCU is a dedicated unit of technical experts whose primary function is to handle catastrophic and large loss claims. Additionally, a referral objective may be displayed in ICMS as shown in Table 2. Consequently, a discussion may take place between the claim handler and the MCM to determine the ESI eligibility and referral to the MCU. For the second distinct group, i.e., the selected ICD-9 codes, an automated ICMS assignment will occur when the ICD-9 code of the claim matches one of the selected ICD-9. Again, a referral objective may then be displayed in ICMS as shown in Table 2.

If the claim factors match more than one automated assignment triggers or claim factors above, each trigger creating the automated assignment can be displayed. For example, if lost time exceeds a predetermined time frame, e.g., 14 days, and the anticipated surgery indicator is present, both referral objectives will be listed. As mentioned earlier, Table 2 shows the automated assignment/referral and re-referral objectives that can be displayed, individually or jointly, in the ICMS.

TABLE 2

| Referral Logic | Referral Objective To Be Displayed |
| --- | --- |
| NOI/POB code combination met | "Nature of Injury/Part of Body description meets medical assignment criteria" |
| Anticipated/performed surgery (A/P/B) | "Surgery is anticipated or has been performed, please assign" |
| Lost time exceeds 14 days | "Patient has not RTW in over 14 days" |
| TT, TP and Medical Incurred total exceeds $20,000 | "The total TT, TP & medical incurreds exceed $20,000" |
| a. Selected ICD-9 codes | a. "The current ICD-9 diagnosis meets medical assignment criteria" |
| b. ESI ICD-9 codes | b. "Claims falls within ESI criteria, please evaluate for medical assignment and referral to MCU" |
| New date disability began | "Patient has begun a new disability period" |

According to an embodiment of the present invention, the medical referral logic of step 4 in FIG. 1 includes claim factors that can prevent an automated assignment to ICMS, and they include: 1) claim is closed in T-MATE; 2) policy coverage=N (none) or U (unknown); 3) controverted indicated=Yes; 4) date of death is populated; 5) there is already an open ICMS referral; 6) the policy is an opted out account; 7) there is a prior carrier policy or excess carrier file; 8) the IW returned to work full duty, or the IW will never RTW; and 9) bypass some controlling offices, i.e., those customer-dedicated offices that have chosen to bypass and not use the medical program of the host insurance carrier or health care plan provider. When the aforementioned claim factors or data fields exist, a negative answer results from step 8, and an automated ICMS assignment will be blocked and the system referral is not sent in step 7. However, a manual medical referral may still be sent by the claim handler in step 6 in some circumstances as a result of the claim handler recognizing the need for medical assignment in step 5. For instance, a customer who may normally use the medical program of the host insurance carrier may request an assignment on a case-by-case basis (usually for serious injuries).

According to an embodiment of the present invention, an automated medical assignment/referral can be prevented—despite the fact that the claim data matches the medical assignment/referral logic in step 8 of FIG. 1, and a generated medical referral is sent to the ICMS roster—if there exists one of previous non-intervened milestones. All claims displayed on the ICMS roster at step 9 will take one of two paths: a) assignment to a MCM; or b) non-intervention. For MCM assignment, if all claim factors are updated in T-MATE as claim facts change, and the claim requires medical management, the MCM will complete the case assigned/case received and sent activity and assign the claim to a nurse in step 11. The "case assigned" activity: 1) is used to create a diary for the medical personnel, e.g., a nurse, to whom the claim is assigned; 2) is marked completed with the result code "case received" by the nurse to whom the claim is assigned, which creates the referral-opened-by-medical milestone; 3) is not used when a claim is non-intervened; and 4) is not used for the sole purpose of removing a claim from the ICMS roster. The "sent" activity happens when the nurse sends the claim activity to T-MATE to become part of the claim notes.

If the SAC instructions require pre-approval prior to managing the claims, the dedicated MCM to the account should seek pre-approval from the customer, prior to completing the case assigned/case received activity. To further streamline the assignment process, nurses can be designated to specific market, employer-dedicated claim units, and/or alpha-split claim units to allow them to remove their own claims from the ICMS roster. Alpha split claim units are those tasked with assigning claim notices to the claim handlers based on alphabetical split of the customer name; for example, one claim handler or adjuster may manage customers with first letter A to G in their names. According to the present invention, the ICMS will not automatically create assignments directly to individual nurses.

For non-intervention of a claim sent to the ICMS roster, there are three distinct reasons such claim may be non-intervened, i.e., three non-intervened milestones:

1. The claim does not meet medical assignment criteria in step 12, when reviewed by the MCM in step 10. Here, a result code of "Non-intervene, does not meet criteria" will display in ICMS. The MCM can also add a note with the specific rationale as to why the claim does not require medical assignment. This will allow for future analysis and enhancements to the assignment logic. For instance, a claim may have met the referral logic because the claim data was not updated, where it appeared that there was an open disability, but the injured employee had returned to work; or the claim met the referral logic but the severity was very low, such as the surgery performed was to suture a cut hand and there was minimal time loss for work.

2. SAC instructions indicate that the customer does not want medical management assigned. Here, a result code of "Non-intervene per customer request" will display in ICMS.
3. Claim is a CAT and MCU has assigned an external resource. Here, a result code of "Non-intervene CAT" will display in ICMS.

If one of the aforementioned non-intervened milestones exists, the claim is not assigned to a nurse to manage, as shown in step 13. T-MATE claim data is then updated as claim facts change, as shown in step 14, and the workflow is started at step 8 again.

As noted in the goals and benefits of the enhanced medical triage of the present invention, manual medical referrals are retained for the claim handlers, as shown in steps 5 and 6 of FIG. 1. In other words, claim handlers maintain the ability to manually refer a claim to ICMS that does not meet the automated assignment logic, and requires medical intervention. As with the automated medical referral/assignment, the claim is reviewed by the MCM at step 10 to determine whether the claim meets the assignment criteria, and the workflow of FIG. 1 continues as mentioned earlier with regard to steps 11-14. Claims sent manually by the claim handlers at steps 5 and 6 may include CM claims and CB claims. Appendix G shows a table detailing the key data elements to manually determine medical assignment.

The medical claim assignments found on the ICMS roster include CB claims, CM-Plus claims, and CM claims. The CB claims include claims that meet the automated assignment logic & claims that are manually sent by the claim handler through the T-MATE Medical referral screen process. The CM-Plus claims are those CM claims that are identified as potentially requiring medical management, due to the type injury and/or treatment, and include those claims that meet the CM-Plus referral logic and the customer has elected to use the CM-Plus product. The CM-Plus referral logic includes repetitive trauma, carpal tunnel, knee injuries, and back injuries with ongoing physical therapy or chiropractic treatment. CM-Plus claims may require review and an assignment decision because the assigned medical personnel, such as an assigned nurse, may need to review for the potential to positively impact the claim outcome due to the medical management charge to the claim file. The review often requires the nurse to contact the treating physician to determine the medical status of the IW. CM claims include only those claims that are manually sent by the claim handler through the T-MATE Medical referral screen process.

In order to maintain the early intervention and quick turnaround of medical assignments, one person per service center may be designated to review the ICMS roster periodically at a predetermined interval, e.g., daily, to be sure all claims, either assigned or non-intervened, are periodically removed. As mentioned earlier, all claims sent to ICMS through the automated assignment logic and through the manual medical referral screen process will list a referral objective and be displayed in ICMS in the "Claim Rep Notes" on the Event screen. Appendix F shows the notes that will display in T-MATE when a medical referral is created. These notes will also display in ICMS in the "Claim Rep Notes" on the Event screen.

As part of the continual improvement process, the enhanced medical triage and assignment process is reviewed to assure consistency of assignments from office (AFO) to office by injury type, severity of injury, and potential medical impact. In addition, the goal is to continually decrease the number of unnecessary referrals sent to the medical unit for review, thus increasing efficiency of the medical assignment process. Part of the improvement process is the use of management information reports that are generated based on "milestones" which are created when certain system activities take place. Milestones include: referral (assignment) and closures (non-intervened). These milestones is used to report statistics on AFO acceptance of claims for medical management. Table 3 shows the Referral Type Milestones that are created in T-MATE when various types of referrals are made to ICMS.

TABLE 3

Referral Type Milestones

| Milestone | Description |
| --- | --- |
| Auto referral to Medical | Standard Automated Referral |
| 14-day Auto referral to Medical | Automated Referral when no return to work within 14 days |
| New Disability Auto referral to Medical | Automated Referral when new Date Disability Began is entered |
| Manual Referral to Medical | Manual Medical Referral |
| Nurse Referral to Medical | Nurse opens claim in ICMS and T-MATE sends back a referral |

Table 4 shows the referral-opened-by medical milestone, which is created in T-MATE when "case assigned"/"case received" is completed in ICMS.

TABLE 4

Referral-Opened-by-Medical Milestone

| Milestone | Description |
| --- | --- |
| Referral opened by medical {Case Assigned/Case Received} | Referral has been accepted for Medical Management. |

Table 5 shows the non-intervened milestones that are created in T-MATE when specific result codes noted below are used with the activity "Cease Activity" in ICMS. Non-intervened result codes are not appropriate when closing a claim after medical management has been initiated. Closure codes such as "Adjuster Requests Closure" are more appropriate when the claim has been initially managed and then requires closure.

TABLE 5

Non-intervened Milestones

| Milestone | Description |
| --- | --- |
| Non-intervened by Medical - Does not meet criteria {cease activity/non-intervene - does not meet criteria} | Non-intervened by Medical as claim would not benefit from medical intervention. |
| Non-intervened by Medical per Customer Request {cease activity/non-intervene per customer request} | Non-intervened by medical on this specific claim as requested by customer |
| non-intervened by medical - CAT {cease activity/non-intervene CAT} | Non-intervened - catastrophic claim which MCU will manage |

Additionally, the referral objectives for both automated and manual referrals are reviewed to determine if the claim requires ongoing medical case management, or utilization review/pre-certification only. The manual referral displays the primary service requested which includes telephonic case management, UR only, or on-site medical or vocational. The referral will also indicate an UM or surgical referral if the referral includes a current treatment request. Ongoing medical management, rather than pre-cert/UR only is considered any time there is ongoing lost time and/or medical treatment. This includes manual and automated referrals.

Figure 4:
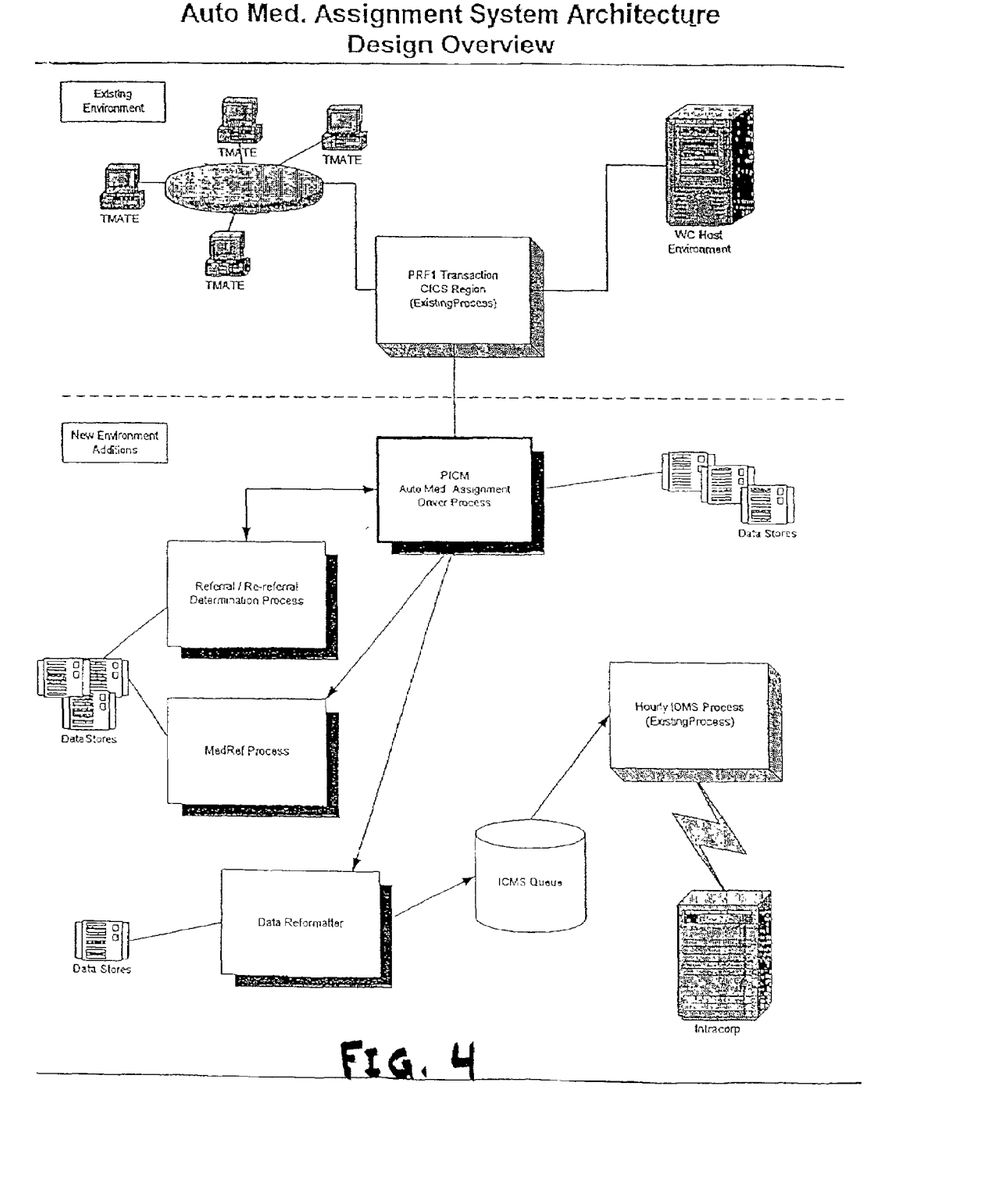
FIG. 4 depicts the existing system environment and the new system environment additions for implementing the enhanced medical triage in accordance to one embodiment of the present invention.

FIG. 4 shows the existing system environment (top part of the figure) for the current medical referral/assignment process and the new system environment additions (bottom part of the figure) to implement the enhanced medical triage of the present invention. The PICM Auto Medical Assignment driver is a traffic router and a driver for the automated medical assignment system process. It is initiated first, filters through preliminary edits, and initiates other components that conduct more detailed and specialized functions. The components initiated by the PICM return control back to the PICM and provide a return message. The PICM then interrogates the message to determine the appropriate next step to conduct for the entire process. The Referral/Re-referral is one of the components initiated by the PICM. It performs all of the triage/assignment edits that have been stored in various data stores. Its basic functions is to determine if a claim needs to be sent to medical either for the first time or as a re-referral. This decision point is triggered when a triage/assignment edit exists. Once a decision is made, it returns control to the PICM driver component and passes a return message. The MedRef Process component is another component initiated by the PICM for two functions: 1) whenever a new referral or a re-ferral is required to by processed; and 2) whenever the system must determine if data has changed in the WC claim system that needs to be propagated into the medical system, so that both system can be in sync with its data. Once processing is complete it returns control to the PICM driver component and passes a return message. The Data Reformatter process component is also initiated by the PICM, and its function is to format a referral/re-referral message or a data update message to be sent to the medical system. It also reads the data stores, gathers the data, builds a message to conform to a specified layout, and places this message onto the ICMS queue component. The data from the ICMS queue is then forwarded via an existing hourly ICMS process to a medical vendor, such as Intracorp, for processing of the claims.

In summary, the enhanced medical triage of the present invention maintains early intervention by the system review of referrals, in addition to creating assignment logic to send only those claims to medical review that require medical intervention. The enhanced medical triage is based on a detailed study of claim data elements, actuarial study, and predictive modeling was reviewed and modeled after the medical supervisor review process. The benefits to this approach are to improve consistency and quality of medical assignments from office to office, and to reduce the unnecessary referrals to ICMS. In addition, the claim handler maintains the ability to manually assign a claim to the medical unit at any time. Furthermore, with turn-overs of claim personnel, inconsistent claim handling and referrals may arise with new claim personnel coming into the job with different opinions and/or different sets of experience. The enhanced medical triage of the present invention allows the new claim personnel to build the body of knowledge of previous personnel, instead of having to start over and provides more consistency between personnel, between offices, and between jurisdictions (because health care plans such as workers compensation plans are state-driven and statutory-driven). Employers will benefit from reduced claim costs, early intervention by claim handlers, and consistency of medical case assignment. This puts the employer in the position where selected lost time claims that have the potential for the greatest medical impact are assigned automatically once compensibility is established.

Although the invention has been described with reference to these preferred embodiments, other embodiments could be made by those in the art to achieve the same or similar results. Variations and modifications of the present invention will be apparent to one skilled in the art based on this disclosure, and the present invention encompasses all such modifications and equivalents.

APPENDIX A

Common Triage/Assignments Decision Points Utilized in Today's ICMS Environment

1. Date of Injury (DOI) → If DOI already exceeds a predetermined period of time, e.g., 14 days, immediate medical assignment should be made.
2. Special Account Communication (SAC) instruction review → Follow customer request from SAC instructions for medical assignment (SAC instructions refer to customer-specific service requirements that the claim professional must meet in handling the claim). For accounts with SACs related to medical assignment pre-approval, up to 50% of the triage time is related to SAC compliance.
3. Diagnosis/ICD-9 (if available) → The following diagnoses are medically assigned the majority of the time (can also be derived from NCCI injury and body part codes):
   Backs
   Necks/disc involvement
   Shoulder/rotator cuffs
   Knee injuries
   Repetitive injuries
   Hernia 50% assignment;
   Wherein ICD-9 refers to the International Classification of Diseases, Ninth Revision; and NCCI refers to the National Council on Compensation Insurance.
4. History of prior injury and pre-existing conditions.
5. Work status → If out of work (OOW), then assign; if modified work duty, then 50% assignment.
6. Type of ICMS referral → If manual by adjuster, then assign; If automated to ICMS, then perform triage.
7. All claims where surgery is anticipated.
8. When there is a request for medical services, for all therapy, diagnostics, DME, etc.
9. Red flags present, e.g., no follow up doctor visit and OOW, multiple claim history, out of network provider, injured worker (IW) in need of physician referral.
10. Description of IW's job (e.g., heavy, repetitive)
11. If modified duty is available, and if RN can assist in identifying modified duty.
12. Disability duration, as outlined in medical protocols (limited use).

APPENDIX B

Data Elements for Mining

CARR market code (or any market code)
ICMS referral date
ICMS manual (MedRef) indicator
ICMS assignment date
Job class code
Job hazard index code
Loss designator
Loss designator level indicator
Second injury indicator
Education level
Work level (i.e., heavy, light, sedentary)
Light work available (Y/N)
Occupational risk indicator (i.e., Char(1); L - light; M - medium; H - heavy, blank)
Probability of permanent injury (i.e., Char(1); L - low; M - medium; H - high; N - none; blank)
Controverted indicator
MIRA factors

APPENDIX B-continued

Data Elements for Mining

Selected system data items:

1. AFO code
2. Claim number
3. Adjusting state
4. Date of NOL (Notice of Loss)
5. SIC code (Standard Industry Classification)
6. Employee Sex
7. Initial treatment code
8. Full/Part time indicator
9. Date of birth
10. Injured worker type
11. Wok days per week
12. Average weekly wage
13. Overtime indicator
14. Date of hire
15. Length of employment - years
16. Accident date
17. Date reported to employer
18. Lost time indicator
19. Return to work indicator
20. Return to work date
21. Fatality indicator
22. Date of death
23. Last day worked
24. Cause code
25. Part of body (POB) code
26. Nature of injury (POI) code
27. Previous injury indicator
28. First aid indicator
29. Hospital indicator
30. Physician indicator
31. Ambulance indicator
32. First Aid date
33. Hospital first date of treatment
34. Hospital length of stay
35. Physician First date of treatment
36. Physician's specialty.

APPENDIX C

Data Mining Results and Data Integrity

| Variable | All Claims | Average | Count | Percent (%) |
|---|---|---|---|---|
|  | Days_NOL | 28.38 | 6570 |  |
| 1 | T_NOL_Date | 1.0 | 6570 | 100 |
| 2 | T_Adj_State | 1.0 | 6570 | 100 |
| 3 | T_Cov_Ver_Ind | 1.0 | 6570 | 100 |
| 4 | T_First_Aid_Ind | 1.0 | 814 | 12 |
| 5 | T_Hosp_Ind | 1.0 | 4537 | 69 |
| 6 | T_Phys_Ind | 1.0 | 1454 | 22 |
| 7 | T_Work_Days_Week | 1.01 | 6570 | 100 |
| 8 | T_DOL | 1.02 | 6570 | 100 |
| 9 | T_Part_Body | 1.03 | 6569 | 100 |
| 10 | T_Gender | 1.03 | 6569 | 100 |
| 11 | T_Cause_Injury | 1.03 | 6570 | 100 |
| 12 | T_Reg_Work_Status | 1.04 | 6192 | 94 |
| 13 | T_Nature_Injury | 1.05 | 6570 | 100 |
| 14 | T_Initial_Treat_Code | 1.10 | 5794 | 88 |
| 15 | T_Rept_Employer_Date | 1.10 | 6567 | 100 |
| 16 | T_Claimant_Zip | 1.17 | 6516 | 99 |
| 17 | T_DOB | 1.32 | 6349 | 97 |
| 18 | T_Policy_Num | 1.33 | 6463 | 98 |
| 19 | T_CARR_Market | 1.42 | 6393 | 97 |
| 20 | T_Hire_Date | 1.42 | 5632 | 86 |
| 21 | T_Sailor_Acct_Num | 1.43 | 5175 | 79 |
| 22 | T_Lost_Time_Ind | 1.47 | 5820 | 89 |
| 23 | T_Prev_Injury_Ind | 1.75 | 6310 | 96 |
| 24 | T_Loss_Des | 1.99 | 6570 | 100 |
| 25 | T_Subro_Flag | 3.46 | 6401 | 97 |
| 26 | T_Ret_Work_Ind | 3.47 | 5686 | 87 |
| 27 | T_Cum_Trauma_Ind | 3.61 | 6399 | 97 |

APPENDIX C-continued

Data Mining Results and Data Integrity

| Variable | All Claims | Average | Count | Percent (%) |
|---|---|---|---|---|
| 28 | T_AWW | 4.08 | 5783 | 88 |
| 29 | T_Last_Day_Worked | 4.25 | 3620 | 55 |
| 30 | T_Level_Ind | 4.89 | 5433 | 83 |
| 31 | T_Cat_Code | 4.91 | 573 | 9 |
| 32 | T_Salary_Cont | 5.14 | 5514 | 84 |
| 33 | T_Cat_Ind | 5.18 | 5463 | 83 |
| 34 | T_Educ_Level | 5.77 | 371 | 6 |
| 35 | T_Contro_Ind | 6.32 | 4936 | 75 |
| 36 | T_ICMS_Ref_Date | 6.63 | 3573 | 54 |
| 37 | T_Light_Work_Avail_Ind | 6.65 | 1984 | 30 |
| 38 | T_Marital_Status | 7.49 | 2409 | 37 |
| 39 | T_Non_Inter_Med_Date | 7.74 | 2142 | 33 |
| 40 | T_Sec_Injury_Ind | 8.39 | 1377 | 21 |
| 41 | T_Litig_Antic_Ind | 8.77 | 4989 | 76 |
| 42 | T_Antic_Med_Mang | 9.00 | 4207 | 64 |
| 43 | T_Occ_Risk_Ind | 9.02 | 4966 | 76 |
| 44 | T_Ret_Work_Data | 9.08 | 1659 | 25 |
| 45 | T_Job_Class_Code | 9.11 | 5111 | 78 |
| 46 | T_Comp_Rate | 9.14 | 5084 | 77 |
| 47 | T_Surg_Antic_Ind | 9.30 | 4899 | 75 |
| 48 | T_ICMS_Assign_Date | 10.04 | 1649 | 25 |
| 49 | T_Ret_Work_Qual | 10.44 | 1513 | 23 |
| 50 | T_Prob_Perm_Inj | 11.63 | 4656 | 71 |
| 51 | T_DOD | 11.94 | 380 | 6 |
| 52 | T_ref_Clsd_Med_Date | 17.91 | 443 | 7 |

APPENDIX D

NCCI NOI/POB Codes

| NOI | Do Not Assign |
|---|---|
| 1 | no physical injury |
| 3 | angina pectoris |
| 54 | asphyxiation |
| 30 | freezing |
| 31 | hearing loss or impairment |
| 32 | heat prostration |
| 36 | infection |
| 37 | inflammation |
| 53 | syncope |
| 55 | vascular |
| 58 | vision loss |
| 60 | dust disease |
| 61 | asbestosis |
| 62 | black lung |
| 63 | byssinosis |
| 64 | silicosis |
| 65 | respiratory disorders |
| 66 | poisoning - chemicals |
| 67 | poisoning - metal |
| 68 | dermatitis |
| 69 | mental disorder |
| 70 | radiation |
| 71 | all other occupational disease |
| 72 | loss of hearing |
| 73 | contagious disease |
| 76 | VDT |

| NOI | Small 100% Assignment |
|---|---|
| 7 | concussion |
| 13 | crushing |
| 22 | enucleation |
| 25 | foreign body |
| 42 | poisoning |
| 41 | myocardial infarction |
| 74 | cancer |
| 75 | aids |
| 77 | mental stress |
| 90 | mult physical injuries |

APPENDIX D-continued

NCCI NOI/POB Codes

| NOI | | Recommendation | POB | |
|---|---|---|---|---|
| 91 | | mult inj/phys & psych | | |

| Large NOI Numbers | | Recommendation | POB | |
|---|---|---|---|---|
| 10 | contusion | include | 10 | mult head inj |
| | | | 11 | skull |
| | | | 12 | brain |
| | | | 20 | mult neck inj |
| | | | 21 | vertebrae |
| | | | 22 | neck disc |
| | | | 25 | neck soft tissue |
| | | | 30 | multiple upper extremities |
| | | | 38 | shoulder |
| | | | 42 | lower back |
| | | | 43 | trunk disc |
| | | | 53 | knee |
| | | | 63 | lumbar & sacral vert |
| | | | 91 | body systems |
| 40 | laceration | include | 11 | skull |
| | | | 13 | ears |
| | | | 20 | mult neck inj |
| | | | 26 | trachea |
| | | | 34 | wrist |
| | | | 38 | shoulder |
| | | | 90 | mult body parts |
| | | | 91 | body systems |
| 49 | sprain | include | 22 | neck disc |
| | | | 30 | mult upper extemities |
| | | | 31 | upper arm |
| | | | 38 | shoulder |
| | | | 39 | wrist & hand |
| | | | 40 | mult trunk |
| | | | 42 | lower back |
| | | | 43 | trunk disc |
| | | | 47 | trunk spinal cord |
| | | | 51 | hip |
| | | | 52 | upper leg |
| | | | 53 | knee |
| | | | 90 | mult body parts |
| | | | 91 | body systems |
| 52 | strain | include | 11 | skull |
| | | | 21 | vertebrae |
| | | | 22 | neck disc |
| | | | 25 | neck soft tissue |
| | | | 30 | mult upper extemities |
| | | | 31 | upper arm |
| | | | 32 | elbow |
| | | | 33 | lower arm |
| | | | 34 | wrist |
| | | | 38 | shoulder |
| | | | 39 | wrist & hand |
| | | | 41 | upper back |
| | | | 42 | lower back |
| | | | 43 | trunk disc |
| | | | 52 | upper leg |
| | | | 53 | knee |
| | | | 63 | lumbar & sacral vert |
| | | | 90 | mult body parts |
| 59 | all other spec. inj., NOC | include | 10 | mult head inj |
| | | | 12 | brain |
| | | | 22 | neck disc |
| | | | 23 | neck spinal cord |
| | | | 38 | shoulder |
| | | | 39 | wrist & hand |
| | | | 41 | upper back |
| | | | 42 | lower back |
| | | | 43 | trunk disc |
| | | | 50 | mult lower extremities |
| | | | 51 | hip |
| | | | 53 | knee |
| | | | 63 | lumba r &sacral vert |
| | | | 90 | mult body parts |

| Investigated NOI by POB | | Rec'dation | POB | |
|---|---|---|---|---|
| 2 | amputation | include all | | |
| 4 | burn | include | 40 | multiple trunk |
| | | | 50 | multiple lower extremities |
| | | | 52 | upper leg |
| | | | 61 | abdomen incl groin |
| | | | 90 | multiple body parts |
| 16 | dislocation | incl. all but | 36 | finger |
| | | | 37 | thumb |
| | | | 56 | foot |
| | | | 57 | toes |
| | | | 58 | great toe |
| 19 | electric shock | include | 11 | skull |
| | | | 35 | hand |
| | | | 90 | mult body parts |
| | | | 91 | body systems |
| 28 | fracture | incl. all but | 16 | teeth |
| | | | 18 | head soft tissue |
| | | | 35 | hand |
| | | | 36 | finger |
| | | | 37 | thumb |
| | | | 44 | chest |
| | | | 45 | sacrum & coccyx |
| | | | 57 | toes |
| | | | 58 | great toe |
| | | | 62 | buttocks |
| | | | 64 | artificial appliance |
| 34 | hernia | include | 20 | multiple neck injury |
| | | | 21 | vertebrae 22 neck disc |
| | | | 42 | lower back |
| | | | 43 | trunk disc |
| | | | 61 | abodomen Incl. Groin |
| 43 | puncture | include | 13 | ears |
| | | | 14 | eyes |
| | | | 48 | internal organs |
| | | | 91 | body systems |
| 46 | rupture | incl. all but | 36 | finger |
| | | | 37 | thumb |
| | | | 54 | lower leg |
| 47 | severance | include all | | |
| 78 | carpal tunnel | include all | | |
| 80 | all other cumulative injury | include | 20 | mult neck inj |
| | | | 21 | vertebrae |
| | | | 22 | neck disc |
| | | | 30 | mult upper extremities |
| | | | 31 | upper arm |
| | | | 32 | elbow |
| | | | 34 | wrist |
| | | | 38 | shoulder |
| | | | 39 | wrist & hand |
| | | | 40 | multiple trunk |
| | | | 41 | upper back |
| | | | 53 | knee |
| | | | 56 | foot |
| | | | 90 | mult body parts |

APPENDIX E

Sample List of Selected ICD-9 Codes

| ICD-9 Code | ICD-9 Description |
|---|---|
| 308.3 | acute stress react nec |
| 308.9 | acute stress react nos |
| 309.81 | prolong posttraum stress |
| 337 | idiopath auto neuropathy |
| 337.2 | reflex sympat dystrophy |
| 337.2 | reflex symp dystroph nos |
| 337.21 | ref symp dyst upper limb |
| 337.22 | ref symp dyst lower limb |
| 337.29 | reflex symp dystroph nec |
| 353.1 | lumbosacral plex lesion |
| 353.2 | cervical root lesion nec |
| 353.3 | thoracic root lesion nec |

APPENDIX E-continued

Sample List of Selected ICD-9 Codes

| ICD-9 Code | ICD-9 Description |
|---|---|
| 353.4 | lumbsacral root les nec |
| 354 | carpal tunnel syndrome |
| 354 | mononeuritis upper limb |
| 354.1 | median nerve lesion nec |
| 354.2 | ulnar nerve lesion |
| 354.3 | radial nerve lesion |
| 354.4 | causalgia of upper limb |
| 354.5 | mononeuritis multiplex |
| 354.8 | mononeuritis arm nec |
| 354.9 | mononeuritis arm nos |
| 550 | inguinal hernia |
| 550 | unilating hernia w gang |
| 550.1 | unilating hernia w obst |
| 550.12 | bilating hernia w obst |
| 550.9 | unilatinguinal hernia |
| 550.9 | inguinal hernia nos |
| 550.92 | bilatinguinal hernia |
| 553 | other abdominal hernia |
| 553 | femoral hernia |
| 553 | unilat femoral hernia |
| 553.02 | bilateral femoral hernia |
| 553.1 | umbilical hernia |
| 553.2 | ventral hernia nos |
| 553.2 | ventral hernia |
| 553.21 | incisional hernia |
| 553.29 | ventral hernia nec |
| 553.3 | diaphragmatic hernia |
| 553.8 | hernia nec |
| 553.9 | hernia nos |
| 682.4 | cellulitis of hand |
| 6826 | cellulitis of leg |
| 682.7 | cellulitis of foot |
| 6829 | cellulitis nos |
| 715 | general osteoarthrosis |
| 715.15 | loc prim osteoart-pelvis |
| 715.16 | loc prim osteoart-l/leg |
| 715.91 | osteoarthros nos-shlder |
| 715.92 | osteoarthros nos-up/arm |
| 715.93 | osteoarthros nos-forearm |

APPENDIX F

Medical Referral Notes

Med Referral Information:
The employee's SSN is ______
The employee is __ (Male/Female)    Date of Birth: _/_/_
Occupation: ______
Date of loss: _/_/_
This a surgical referral.   OR   This is a non-surgical referral.
Primary service requested: ______
Medical information: (followed by at least one of the following 5 lines)
Physical therapy is requested.
Chiropractic is requested.
Diagnostic tests are requested.
No medical requests.
Injury description: ______/______
Cause: ______
Nature: ______
An IME has been performed.   OR   An IME has not been performed.
Current Treating physician: ______
Phone: (__)__-__  Address: ______
Modified duty is available.   OR   It is unknown whether modified duty is available.   OR   Modified duty is not available.
The employee is currently out of work since _/_/_
OR   They employee is currently working
SAC Text, if any.
Med Referral Objective:
Comments/Referral Objective:

APPENDIX G

Manual ICMS Triage Process

| Data | Source of Data | Timing/Availability |
|---|---|---|
| Work Status - if OOW or on modified duty:<br>A. Actual lost time > 14 days<br>B. Anticipated lost time > 14 days<br>C. Modified duty > 14 days | T-MATE/Host | NOL Updated after initial claim contacts |
| SAC | Claim Reference Library | SAC language and SAC coding impacting ICMS referrals requires updating |
| Diagnosis | Claim notes only. Note: the nature of injury listed may be viewed as the diagnosis | ICD-9 not displayed in T-MATE. Diagnosis is found to frequently be missing (in notes) at initial stage. Dx confirmed at 1st medical bill. |
| ICMS Protocols - to determine disability duration | ICMS | Once diagnosis is known, protocols may be used to estimate disability period |
| IW's job category or description of physical demand category | Job Class code - T-MATE<br>Job title - T-MATE/ICMS<br>DOT/Job category - ICMS | Job Class - MIRA factor<br>Title - NOL<br>Job category (i.e., sedentary, light, etc.) derived from DOT code |
| Treating physician look for network status or specialty of MD | T-Mate - C & I screen, directory & notes<br>ICMS - Med Ref | At NOL - often missing or inaccurate information available at triage |
| Red Flags present: | | |
| A. Prior injury to same body part | T-MATE | MIRA factor |
| B. Age > 55 | | |
| C. Employee hospitalized | T-MATE | MIRA |
| D. Pre-existing condition | Notes | |
| E. Lay-off status/ seasonal worker | | |
| F. Date of Hire | T-MATE | MIRA |
| | T-MATE | MIRA |
| | T-MATE | MIRA |
| Compensability status | T-MATE | After ICU/RTW determination |
| Anticipated surgery | Notes/protocols | At MD contact |
| Expected or requested treatment (need for pre-cert/UR or watch Tx) | Notes/derived from protocols | At MD contact |

The invention claimed is:

1. A computer implemented and user assisted method for providing medical referrals and medical assignments to medical insurance claims, comprising:
   receiving by a claim handler a reported medical insurance claim and collecting by the claim handler data related to the reported medical insurance claim;
   forwarding the reported medical insurance claim and the collected data relating to the reported claim to medical referral logic;
   automatically performing the medical referral logic on the reported medical insurance claim and the collected data to determine whether a medical referral is warranted based upon predetermined referral criteria;
   when the medical referral is warranted, automatically forwarding the reported medical insurance claim and the collected data to a medical case management system for review by a medical case manager;

when the medical referral is not warranted, preventing the reported medical insurance claim and the collected data from being referred to the medical case management system;

when the medical referral is warranted and the reported medical insurance claim is reviewed by the medical case manager, assigning the reported medical insurance claim by the medical case manager to a medical personnel when the assignment is warranted based upon predetermined assignment criteria;

collecting updated data relating to the reported medical insurance claim when the data changes and when the updated data is present;

performing the medical referral logic on the reported medical insurance claim and the updated collected data to determine whether a medical referral is warranted based upon the predetermined referral criteria; and when the medical referral is warranted, automatically forwarding the reported medical insurance claim and the updated collected data to a medical case management system for review by a medical case manager to determine whether to assign the reported medical insurance claim to the medical personnel.

2. The method of claim 1, wherein the medical insurance claim is reported from a telephone reporting center to a claim service office via a claim management system.

3. The method of claim 1, wherein the medical referral logic comprises analyzing previous claims that are similar to the reported medical insurance claim and their medical referrals and assignments.

4. The method of claim 3, wherein analyzing the previous similar claims and their medical referrals and assignments comprises:

preparing a list of data elements relating to the previous similar claims;

capturing the data elements from the prepared list; and determining when at least one of the captured data elements is populated.

5. The method of claim 1, wherein the automatically performing medical referral logic comprises:

preparing a main list of combinations of a plurality of nature of injury (NOI) data and a plurality of part of body (POB) data on which the plurality of NOI are associated;

selecting from the main list a sub-list having combinations of one of the plurality of NOI and an associated one of the plurality of POB that desire medical referral (NOI/POB);

comparing the reported claim and the collected data with the sub-list of combinations of NOI/POB; and determining that the medical referral is warranted when the reported claim and the collected data match with at least one of the sub-list of combinations of NOI/POB.

6. The method of claim 1, wherein the automatically performing medical referral logic comprises:

assessing the reported claim and the collected data to determine whether there is at least one of an indication of anticipated surgery, and an indication of surgery already performed on the reported claim; and determining that the medical referral is warranted when there is at least one of the indication of anticipated surgery, and the indication of surgery already performed on the reported claim.

7. The method of claim 1, wherein the automatically performing medical referral logic comprises:

determining whether there is a new date which disability began for the reported claim; and determining that the medical referral is warranted when there exists the new date which disability began.

8. The method of claim 1, wherein the automatically performing medical referral logic comprises:

determining whether a sum of TT incurred, TP incurred, and medical incurred is greater than a predetermined monetary value; and determining that the medical referral is warranted when the sum is greater than the predetermined monetary value.

9. The method of claim 1, wherein the automatically performing medical referral logic comprises:

preparing a main list of ICD-9 codes for which the medical referral is warranted;

determining whether the reported claim and the collected data include one of the ICD-9 codes in the main list of ICD-9 codes; and determining that the medical referral is warranted when the reported claim and the collected data include one of the ICD-9 codes in the main list of ICD-9 codes.

10. The method of claim 9, wherein preparing the main list of ICD-9 codes for which the medical referral is warranted comprises:

preparing a first sub-list having selected ICD-9 codes which identify claims with significant medical issues that require medical attention; and preparing a second sub-list having ICD-9 codes of early strategic intervention, which denote a desire to medically intervene.

11. The method of claim 1, wherein the reported claim relates to an injury sustained by an individual; and wherein automatically performing medical referral logic comprises:

assessing the reported claim and the collected data to determine whether the injured individual has not returned to work for more than a predetermined period of time after the injury; and determining that the medical referral is warranted when the injured individual has not returned to work for more than the predetermined period of time after the injury.

12. The method of claim 1, wherein the automatically performing medical referral logic comprises:

assessing the reported claim and the collected data to determine whether there is at least one of an indication of anticipated surgery, and an indication of surgery already performed on the reported claim;

determining whether there is a new date which disability began for the reported claim;

determining whether a sum of TT incurred, TP incurred, and medical incurred is greater than a predetermined monetary value; and preparing a main list of ICD-9 codes for which the medical referral is warranted.

13. The method of claim 1, wherein the medical referral logic comprises specific market or employer resource information.

14. The method of claim 1, wherein the medical referral logic comprises information provided by medical team leaders in local claim service centers regarding (a) current methods of claim evaluation to determine medical referral; and (b) Special Account Communication (SAC) instructions that impact medical referral decisions.

15. The method of claim 1, wherein the medical referral logic comprises analyzing reported medical insurance claims currently being referred and assigned for medical management and claims non-intervened for medical referral.

16. The method of claim 15, wherein analyzing the reported medical insurance claims currently being referred and assigned for medical management and claims non-intervened for medical referral comprises:
preparing a list of data elements relating to the claims;
capturing the data elements from the prepared list; and
determining when at least one of the captured data elements is populated.

17. The method of claim 3 or 15, wherein analyzing the claims comprises:
reviewing one or more of actual paid value, medical incurreds, indemnity incurreds, National Council on Compensation Insurance (NCCI) codes, ICD-9 data of assigned and non-assigned claims, anticipated surgery indicator, and lost time days.

18. The method of claim 1, further comprising:
when the medical referral is warranted, preventing the reported medical insurance claim and the collected data from reaching the medical case management system if any of the following are true:
the claim is closed in the claim management system;
policy coverage is N (none) or U (unknown);
controverted indicator is Yes;
date of death is populated;
there is already an open medical case management system referral;
the policy is an opted out account;
there is a prior carrier policy or excess carrier file;
the injured worker returned to work full duty;
the injured worker will never return to work; or
the medical program of the host insurance carrier or health care plan provider is bypassed.

19. A computer implemented and user assisted method for providing medical referrals and medical assignments to medical insurance claims, comprising:
forwarding a reported medical insurance claim and collected data relating to the reported claim from a claim handler to medical referral logic;
automatically performing the medical referral logic on the reported medical insurance claim and the collected data to determine whether a medical referral is warranted, comprising the steps of:
(1) preparing a main list of combinations of a plurality of nature of injury (NOI) data and a plurality of part of body (POB) data on which the plurality of NOI are associated;
selecting from the main list a sub-list having combinations of one of the plurality of NOI and an associated one of the plurality of POB that desire medical referral (NOI/POB);
comparing the reported claim and the collected data with the sub-list of combinations of NOI/POB; and
determining that the medical referral is warranted when the reported claim and the collected data match with at least one of the sub-list of combinations of NOI/POB, and
(2) assessing the reported claim and the collected data to determine whether there is at least one of an indication of anticipated surgery, and an indication of surgery already performed on the reported claim; and
determining that the medical referral is warranted when there is at least one of the indication of anticipated surgery, and the indication of surgery already performed on the reported claim, and
(3) assessing the reported claim and the collected data to determine whether the injured individual has not returned to work for more than a predetermined period of time after the injury; and
determining that the medical referral is warranted when the injured individual has not returned to work for more than the predetermined period of time after the injury;
when the medical referral is warranted, automatically forwarding the reported medical insurance claim and the collected data to a medical case management system for review by a medical case manager;
when the medical referral is not warranted, preventing the reported medical insurance claim and the collected data from reaching the medical case management system; and
when the medical referral is warranted and the reported medical insurance claim is reviewed by the medical case manager, assigning the reported medical insurance claim by the medical case manager to a medical personnel when the assignment is warranted based upon predetermined assignment criteria.

20. The method of claim 1, further comprising seeking by the medical case manager pre-approval for medical assignment.

21. The method of claim 1, further comprising:
when the medical referral is warranted and the reported medical insurance claim is reviewed by the medical case manager, non-intervening and not assigning the reported medical insurance claim by the medical case manager to a medical personnel when any of the following is true:
the claim does not meet medical assignment criteria;
the account instructions indicate that a customer does not want medical assignment; or
the claim is a catastrophic claim or severe injury.

22. The method of claim 1, further comprising:
forwarding by the claim handler a reported medical insurance claim and collected data relating to the reported claim to a medical case management system for review by a medical case manager.

23. The method of claim 1, further comprising:
generating one or more management information reports based on milestones created when certain system activities take place.

24. The method of claim 1, wherein when the medical referral is warranted and the reported medical insurance claim is reviewed by the medical case manager, preventing the reported medical insurance claim by the medical case manager from being assigned to the a medical personnel when the assignment is not warranted.

25. The method of claim 19, wherein the automatically performing medical referral logic comprises:
assessing the reported claim and the collected data to determine whether there is at least one of an indication of anticipated surgery, and an indication of surgery already performed on the reported claim; and
determining that the medical referral is warranted when there is at least one of the indication of anticipated surgery, and the indication of surgery already performed on the reported claim.

26. The method of claim 19, wherein the medical referral logic comprises:
determining whether there is a new date which disability began for the reported claim; and
determining that the medical referral is warranted when there exists the new date which disability began.

27. The method of claim 19, wherein the medical referral logic comprises:

determining whether a sum of TT incurred, TP incurred, and medical incurred is greater than a predetermined monetary value; and determining that the medical referral is warranted when the sum is greater than the predetermined monetary value.

28. The method of claim 19, wherein the medical referral logic comprises:

preparing a main list of ICD-9 codes for which the medical referral is warranted;

determining whether the reported claim and the collected data include one of the ICD-9 codes in the main list of ICD-9 codes; and determining that the medical referral is warranted when the reported claim and the collected data include one of the ICD-9 codes in the main list of ICD-9 codes.

29. The method of claim 28, wherein the preparing the main list of ICD-9 codes for which the medical referral is warranted comprises:

preparing a first sub-list having selected ICD-9 codes which identify claims with significant medical issues that require medical attention; and preparing a second sub-list having ICD-9 codes of early strategic intervention, which denote a desire to medically intervene.

30. The method of claim 19, wherein the reported claim relates to an injury sustained by an individual; and wherein the automatically performing medical referral logic comprises:

assessing the reported claim and the collected data to determine whether the injured individual has not returned to work for more than a predetermined period of time after the injury; and determining that the medical referral is warranted when the injured individual has not returned to work for more than the predetermined period of time after the injury.

31. The method of claim 19, wherein the automatically performing medical referral logic comprises:

assessing the reported claim and the collected data to determine whether there is at least one of an indication of an anticipated surgery, and an indication of surgery already performed on the reported claim;

determining whether there is a new date which disability began for the reported claim;

determining whether a sum of TT incurred, TP incurred, and medical incurred is greater than a predetermined monetary value; and preparing a main list of ICD-9 codes for which the medical referral is warranted.

32. The method of claim 19, wherein the medical referral logic comprises information provided by medical team leaders in local claim service centers regarding (a) current methods of claim evaluation to determine medical referral; and (b) Special Account Communication (SAC) instructions that impact medical referral decisions.

33. The method of claim 19, wherein the medical referral logic comprises analyzing reported medical insurance claims currently being referred and assigned for medical management and claims non-intervened for medical referral.

34. The method of claim 33, wherein the analyzing the reported medical insurance claims currently being referred and assigned for medical management and claims non-intervened for medical referral comprises:

preparing a list of data elements relating to the claims;

capturing the data elements from the prepared list; and determining when at least one of the captured data elements is populated.

35. The method of claim 19, further comprising:

when the medical referral is warranted, preventing the reported medical insurance claim and the collected data from reaching the medical case management system if any of the following are true:

the claim is closed in the claim management system;

policy coverage is N (none) or U (unknown);

controverted indicator is Yes;

date of death is populated;

there is already an open medical case management system referral;

the policy is an opted out account;

there is a prior carrier policy or excess carrier file;

the injured worker returned to work full duty;

the injured worker will never return to work; or the medical program of the host-insurance carrier or health care plan provider is bypassed.

36. The method of claim 19, further comprising:

when the medical referral is warranted and the reported medical insurance claim is reviewed by the medical case manager, non-intervening and not assigning the reported medical insurance claim by the medical case manager to a medical personnel when any of the following is true:

the claim does not meet medical assignment criteria;

the account instructions indicate that a customer does not want medical assignment; or the claim is a catastrophic claim or severe injury.

37. The method of claim 19, further comprising:

forwarding by the claim handler a reported medical insurance claim and collected data relating to the reported claim to a medical case management system for review by a medical case manager.

38. The method of claim 19, further comprising:

generating one or more management information reports based on milestones created when certain system activities take place.

39. A computer implemented and user assisted method for providing medical referrals and medical assignments to medical insurance claims, comprising:

forwarding a reported medical insurance claim and collected data relating to the reported claim from a claim handler to medical referral logic;

automatically performing the medical referral logic on the reported medical insurance claim and the collected data to determine whether a medical referral is warranted based upon predetermined referral criteria;

when the medical referral is warranted, automatically forwarding the reported medical insurance claim and the collected data to a medical case management system for review by a medical case manager;

when the medical referral is not warranted, preventing the reported medical insurance claim and the collected data from being referred to the medical case management system; and when the medical referral is warranted and the reported medical insurance claim is reviewed by the medical case manager, assigning the reported medical insurance claim by the medical case manager to a medical personnel when the assignment is warranted based upon predetermined assignment criteria and not assigning the reported medical insurance claim by the medical case manager to medical personnel when any of the following is true:

when account instructions are present, and when the account instructions indicate that a customer does not want medical assignment; or the claim is a catastrophic claim or severe injury.

40. The method of claim 1, 19, or 39 wherein the reported medical insurance claim is from a workers compensation insurance carrier, a health insurance carrier, or a health care plan provider.

41. The method of claim 39, wherein the medical referral logic comprises:

assessing the reported claim and the collected data to determine whether there is at least one of an indication of an anticipated surgery, and an indication of surgery already performed on the reported claim; and determining that the medical referral is warranted when there is at least one of the indication of an anticipated surgery, and the indication of surgery already performed on the reported claim.

42. The method of claim 39, wherein the automatically performing medical referral logic comprises:

determining whether there is a new date which disability began for the reported claim; and determining that the medical referral is warranted when there exists the new date which disability began.

43. The method of claim 39, wherein the automatically performing medical referral logic comprises:

determining whether a sum of TT incurred, TP incurred, and medical incurred is greater than a predetermined monetary value; and determining that the medical referral is warranted when the sum is greater than the predetermined monetary value.

44. The method of claim 39, wherein the automatically performing medical referral logic comprises:

preparing a main list of ICD-9 codes for which the medical referral is warranted;

determining whether the reported claim and the collected data include one of the ICD-9 codes in the main list of ICD-9 codes; and determining that the medical referral is warranted when the reported claim and the collected data include one of the ICD-9 codes in the main list of ICD-9 codes.

45. The method of claim 44, wherein preparing the main list of ICD-9 codes for which the medical referral is warranted comprises:

preparing a first sub-list having selected ICD-9 codes which identify claims with significant medical issues that require medical attention; and preparing a second sub-list having ICD-9 codes of early strategic intervention, which denote a desire to medically intervene.

46. The method of claim 39, wherein the reported claim relates to an injury sustained by an individual; and wherein the automatically performing medical referral logic comprises:

assessing the reported claim and the collected data to determine whether the injured individual has not returned to work for more than a predetermined period of time after the injury; and determining that the medical referral is warranted when the injured individual has not returned to work for more than the predetermined period of time after the injury.

47. The method of claim 39, wherein the automatically performing medical referral logic comprises:

assessing the reported claim and the collected data to determine whether there is at least one of an indication of an anticipated surgery, and an indication of surgery already performed on the reported claim;

determining whether there is a new date which disability began for the reported claim;

determining whether a sum of TT incurred, TP incurred, and medical incurred is greater than a predetermined monetary value; and preparing a main list of ICD-9 codes for which the medical referral is warranted.

48. The method of claim 39, wherein the medical referral logic comprises information provided by medical team leaders in local claim service centers regarding (a) current methods of claim evaluation to determine medical referral; and (b) Special Account Communication (SAC) instructions that impact medical referral decisions.

49. The method of claim 39, wherein the medical referral logic comprises analyzing reported medical insurance claims currently being referred and assigned for medical management and claims non-intervened for medical referral.

50. The method of claim 49, wherein the analyzing the reported medical insurance claims currently being referred and assigned for medical management and claims non-intervened for medical referral comprises:

preparing a list of data elements relating to the claims;

capturing the data elements from the prepared list; and determining when at least one of the captured data elements is populated.

51. The method of claim 39, further comprising:

when the medical referral is warranted, preventing the reported medical insurance claim and the collected data from reaching the medical case management system if any of the following are true:

the claim is closed in the claim management system;

policy coverage is N (none) or U (unknown);

controverted indicator is Yes;

date of death is populated;

there is already an open medical case management system referral;

the policy is an opted out account;

there is a prior carrier policy or excess carrier file;

the injured worker returned to work full duty;

the injured worker will never return to work; or the medical program of the host insurance carrier or health care plan provider is bypassed.

52. The method of claim 39, further comprising:

forwarding by the claim handler a reported medical insurance claim and collected data relating to the reported claim to a medical case management system for review by a medical case manager.

53. The method of claim 39, further comprising:

generating one or more management information reports based on milestones created when certain system activities take place.

* * * * *